United States Patent [19]

Hellinger

[11] Patent Number: 4,990,250

[45] Date of Patent: Feb. 5, 1991

[54] REFERENCE FLOW LIQUID CHROMATOGRAPHY SYSTEM WITH STABLE BASELINE

[75] Inventor: Lance Hellinger, San Jose, Calif.

[73] Assignee: Spectra Physics, Inc., San Jose, Calif.

[21] Appl. No.: 456,021

[22] Filed: Dec. 22, 1989

Related U.S. Application Data

[63] Continuation of Ser. No. 155,592, Feb. 12, 1988, abandoned.

[51] Int. Cl.$^5$ .............................................. B01D 15/08
[52] U.S. Cl. ................................. 210/198.2; 210/101; 73/61.1 C; 422/70
[58] Field of Search ............ 210/656, 659, 101, 198.2; 422/70; 436/161; 73/61.1 C

[56] References Cited

U.S. PATENT DOCUMENTS

| | | | |
|---|---|---|---|
| 3,458,437 | 7/1969 | Ouano | 210/659 |
| 3,847,550 | 11/1974 | Scott | 210/659 |
| 4,016,074 | 4/1977 | Porter | 210/659 |
| 4,128,476 | 12/1978 | Rock | 210/101 |
| 4,137,161 | 1/1979 | Shimada | 210/659 |
| 4,271,697 | 6/1981 | Mowery | 210/659 |
| 4,290,776 | 9/1981 | Yamada | 210/659 |
| 4,310,420 | 1/1982 | Konishi | 210/659 |
| 4,311,586 | 1/1982 | Baldwin | 210/101 |
| 4,422,942 | 12/1983 | Allington | 210/659 |
| 4,544,485 | 10/1985 | Pinkerton | 210/198.2 |
| 4,595,495 | 6/1986 | Yotam | 210/101 |
| 4,595,496 | 6/1986 | Carson | 210/101 |

OTHER PUBLICATIONS

Hunkapiller et al., (1980) Science 207: 523–525.
Stevenson et al., (1971) Clinical Chemistry 17(8): 774–781.

Primary Examiner—Ernest G. Therkorn
Attorney, Agent, or Firm—Ronald C. Fish

[57] ABSTRACT

There is disclosed herein an apparatus and method for performing liquid chromatography analysis with a stable baseline. The apparatus utilizes positive displacement means on each of two flow paths and a control system to regulate the flow such that the flow in both flow paths is identical. Only one flow path has sample injected therein. Each flow path is passed through a separate liquid chromatography column and a common detector at the output end of each column. Since one flow path contains solvent only and the other flow path contains both solvent and sample, any changes in the characteristics of the output streams of the liquid chromatography columns caused by changes in the solvent composition itself have a common mode. Therefore, only the difference signal is output from the detector which indicates changes in the characteristics of the output stream of the sample flow path caused solely by the presence of the sample components. By outputting the signal from the detector, a stable baseline may be achieved which takes into account only changes caused by the sample components and not changes caused by alteration of the solvent composition. This allows refractive index detectors to be used with gradient solvent analysis for the first time.

19 Claims, 5 Drawing Sheets

REFERENCE FLOW LIQUID CHROMATOGRAPHY SYSTEM WITH STABLE BASELINE

This application is a continuation of application Ser. No. 07/155,592, filed Feb. 12, 1988, now abandoned.

BACKGROUND OF THE INVENTION

The invention pertains to the field of liquid chromatography, and, more particularly, to the field of pumping systems to control the flow of solvent and sample through liquid chromatography columns.

Liquid chromatography is a process whereby the known components of a sample may be analyzed to determine the quantity of each component in a sample of unknown composition. To make such an analysis, the sample is dissolved in a solvent stream which is then passed through the liquid chromatography column. Liquid chromatography columns contain particles often modified with chemical reagents which act upon the solvent and sample system to retain the various sample components for different amounts of time. In other words, as the sample is pumped through the column, the output stream is comprised of the basic solvent which carries the sample plus the individual components of the sample which emerge from the output of the column at different times.

Liquid chromatography analysis systems detect the presence of the various components of the sample in the output stream using various types of detectors. The purpose of these detectors is to record characteristics of the output streams and to generate signals in the form of output waves (spikes) which represent the presence and quantity of each particular sample component. Each of these spikes appears in the output stream at a different time. The time of occurrence of each spike indicates which component of the sample is then emerging. These "retention" times are based upon the known characteristics of each sample component and the known characteristics of the liquid chromatography column in acting upon that component. However, these retention times are also based upon assumptions as to the magnitude of the flow rate of solvent through the column and the relative stability of this flow rate.

Normally, light absorbance detectors are used at the output of the liquid chromatography column to detect changes in light absorbance as sample components emerge. These absorbance detectors depend upon the light absorbance of the sample components in the output stream and generate signals indicative of this absorbance which can be used to quantify the size of the peak.

However, in certain applications, the sample components do not absorb light. In these applications, detectors such as refractive index, fluorescence, conductivity, electrochemical and other types of detectors are used to quantify the peaks. Refractive index detectors measure the varying amounts of refraction of a light beam as it passes through the output stream. The amount of refraction or bending of the light beam at any particular time as it passes through the output stream depends upon the refractive index and the magnitude of a particular sample component in the output stream at that time. These detectors output signals which quantify the amount of refraction.

An unfortunate side effect of the use of refractive index detectors is that they are very sensitive to changes in the composition of the solvent carrier. In many applications, it is useful to have solvent compositions with multiple components, and frequently "gradient" solvents are desirable. A gradient solvent is a solvent comprised of two or more solvents where the solvent composition is varied over time. A very popular way of making up gradient solvents is to have each solvent delivered by a separate pump and to run each pump at an appropriate speed to make up the currently desired solvent composition.

Gradient solvent compositions are not used in the prior art where refractive index detectors must be used. Additionally, the use of pump blended solvent mixtures cannot occur with refractive index detectors. The only current method of forming the solvent composition for use with refractive index detectors is to form the solvent composition in a separate container and mixing it thoroughly. This separate process of forming the solvent composition and mixing it thoroughly causes the relative makeup of the solvent composition to be known and nonvarying.

However, this is an inconvenient process for use in commercial liquid chromatography systems and is incompatible with creation of a continuously changing gradient. In commercial liquid chromatography systems, solvent composition makeup is normally done in either of two ways. One way involves using a plurality of valves which gate the various solvent components into the pump which drives the solvent composition through the liquid chromatography column. Another way is through the use of multiple pumps as described above.

However, the reproducibility of the solvent composition which can be formed using either the multiple pump or valve method is not sufficient for use with refractive index detectors. This is because the pumps or valves cannot control the exact composition of the solvent mixture as well as by hand mixing. Most pumps have a repeatability factor of 0.1% which is not high enough for use with refractive index detectors.

Basically, refractive index detectors are so very sensitive to the solvent composition that even the slightest error in the relative magnitude of the quantities of solvent components in the solvent mixture will lead to a phenomenon called "baseline drift". Baseline drift refers to changes in the output signal of the detector which are caused by changes in the solvent composition and not changes in the sample component content of the output stream. Basically, baseline drift is noise which degrades the accuracy of the results which can be obtained by a liquid chromatography system. In an ideal system, the output of the detector at the output of the liquid chromatography column would be a steady state stable value when no sample was injected into the input stream entering the column. However, when solvent makeup valves or individual pump motors for each solvent component are used to make up the solvent composition, the errors in the composition which result cause the baseline to drift erratically because of the extreme sensitivity of the refractive index detectors to the slight changes in the refractive index of the solvent composition itself. The same problem can occur with use of other detectors, but is aggravated when using refractive index detectors.

Another problem with the use of pumps for solvent makeup is that the solvent composition is often not thoroughly mixed. This results in erratic baseline drift also.

Further, with absorbance types of detectors, the absorbance of the solvent itself changes at different wavelengths. This too can result in baseline drift error.

One solution to baseline drift that has been tried in the prior art is to use an insensitive range on the recorder used to record the results of a run. Unfortunately, this limits the sensitivity and resolution of the system. Thus, the use of gradient solvents with refractive index detectors has not been possible in the past and the use of pumps for solvent makeup has not been possible when using refractive index detectors even when gradients were not being used. Further, baseline drift is also a problem with other types of detectors such as absorbance detectors where the wavelength of the light is sensitive to the absorbance characteristics of the solvent components.

Others have attempted to solve the problem of baseline drift in the prior art but have failed. At least two groups of workers in the art have tried dual flow chromatography systems whereby the stream of solvent is split by a T connection in front of the column into two paths. One of these two paths was routed through the column while the other flow path was coupled directly to the common detector reference flow path input. This approach is described by Hunkapillar and Hood in *Science* magazine, Vol. 207, p. 24 (1980) and by Stevenson and Burtis in *Clinical Chemistry*, Vol. 17, page 774 (1971). The problem with this approach is that no positive displacement means is provided for each path. Thus, if differences in the resistance to flow exist between the two flow paths, unequal flow rates exist in each path, and the reference signal will become "out of synchronization" with the sample signal for which the reference signal is supposed to act as a reference. This cause errors.

Accordingly, there has arisen a need for a liquid chromatography system which is free of baseline drift in all applications. Such a system should be able to mix solvent gradients using pumps or solvent makeup valves to make either gradient or constant solvent compositions and be usable with any type of detector including refractive index detectors without errors caused by baseline drift.

SUMMARY OF THE INVENTION

According to the teachings of the invention, there is disclosed herein a method and apparatus for performing either gradient or non-gradient solvent analysis of unknown samples using liquid chromatography systems with any type of detector including refractive index detectors. The basic principle of the invention is the use of two positive displacement, equal flow branches through two independent liquid chromatography columns each of which flows into a common detector which detects the difference between the two output streams characteristics and outputs a signal indicative of the difference. One flow is called the reference flow path and has no sample injected therein and the other flow is called the sample flow path and has sample injected therein. Both paths should be the same length. Because the flow rate in each path is forced to be the same, any error caused by baseline drift in the output of the sample flow carrying the unknown sample can be eliminated by comparison with the reference flow path.

The method according to the teachings of the invention is to use any means possible to force the flow rate in the two paths through two independent liquid chromatography columns to be the same. Thus, even though one liquid chromatography column may have more back pressure than the other, this resistance to the flow is overcome by the positive displacement apparatus in each path thereby forcing the flow rates to be the same.

The apparatus according to the teachings of the invention may have several different embodiments. In the preferred embodiment, a single pump having two separate flow paths is used. This pump may have one, two or three heads. In the two head design, two pistons in the first pump head are input pistons which draw their solvent composition through a T connection from a single solvent composition makeup system comprised of a plurality of makeup valves in a mixing block and a mixture control input for receiving mixture control information. Two check valves for the input piston pair insure that solvent flow is unidirectional into the input pistons and out from the output pistons. The outputs of these two input pistons are individually directed through output check valves to a pair of output pistons in the second pump head. The output of each of these output pistons is connected to the individual liquid chromatography columns in the two independent flow paths. That is, one of the output pistons drives the solvent composition through one of the liquid chromatography columns, while the other piston drives the solvent composition through the other liquid chromatography column. There is a sample injector which injects sample in the solvent stream entering one of the liquid chromatography columns.

The output of each of the liquid chromatography columns is connected to a common detector to detect the peaks occurring in the output stream. The detector uses a simple differential amplifier circuit to subtract the output of the reference flow path from the output of the sample flow path thereby achieving accurate results without baseline drift. A reduction in baseline drift by a factor of 90 has been achieved using the teachings of the invention.

Alternative embodiments for the structure include the use of two separate two-piston pumps which are mechanically driven on the same shaft by the same motor. Each of the pumps drives a separate flow path, but each pump draws its input solvent from a common source.

Another alternative embodiment is the use of two separate pumps which are electronically controlled to have the same flow rate.

DETAILED DESCRIPTION OF THE PREFERRED EMBODIMENT

Figure 1:
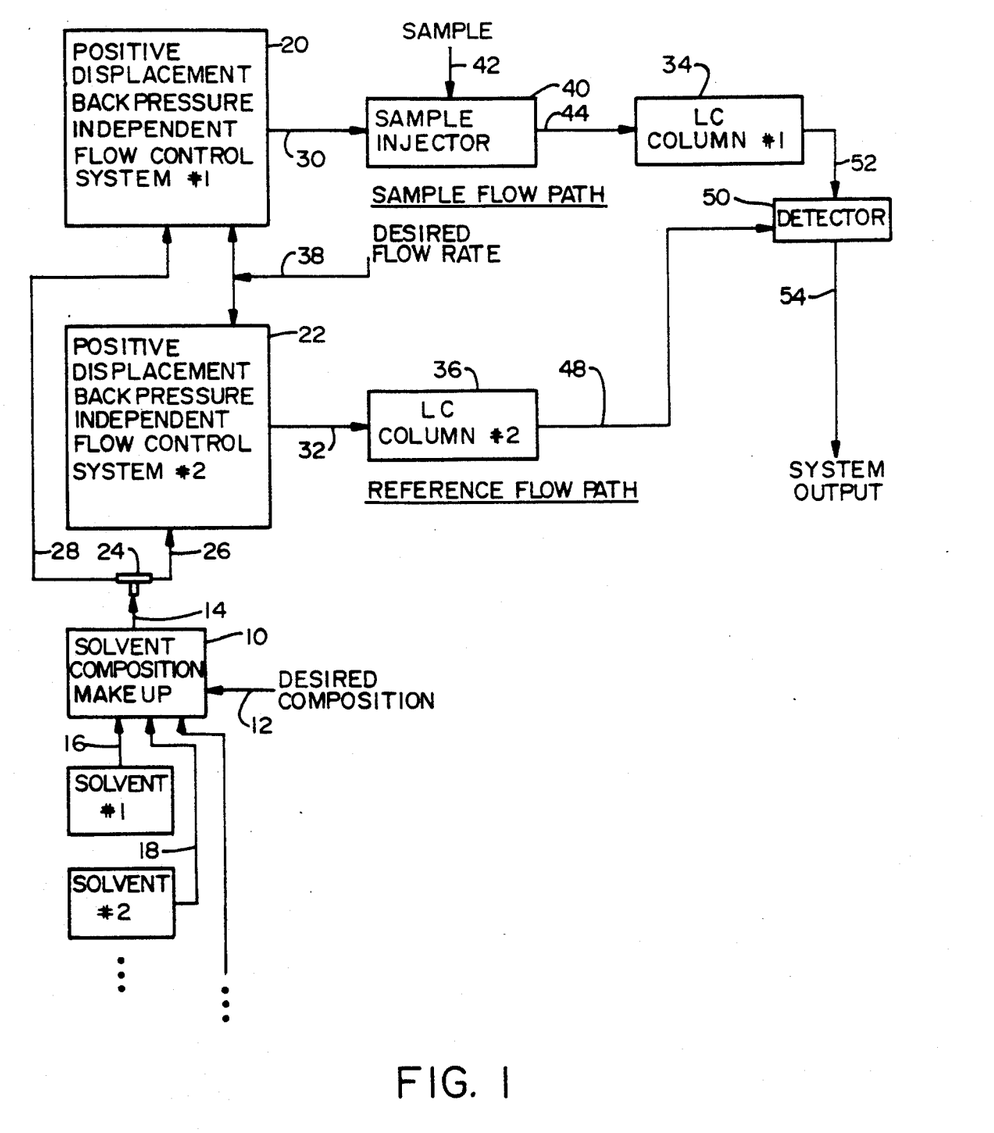
FIG. 1 is a block diagram showing, in schematic form, a generic version of the apparatus of the invention.

Referring to FIG. 1, there is shown a block diagram of a generic system according to the teachings of the invention. A solvent composition makeup block 10 is coupled to a plurality of different solvent sources. This composition makeup block can be any conventional apparatus including a single pump drawing its input from a plurality of solvent composition makeup valves such as the SP8800 Gradient Pump available commercially from the assignee of the present invention. Each of the valves is coupled to a different solvent source. In alternative embodiments, the composition makeup block 10 can be a plurality of individual pumps, each drawing its input from a different solvent source and each being run at a speed which is a function of the desired percentage of that solvent component in the final composition. A desired composition input signal on line 12 defines the desired percentage of each individual solvent element in the final composition in output stream 14. The desired composition signal may be a packet of digital data comprised of one or more bytes defining the desired percentage of a particular solvent composition element. In other embodiments, the solvent composition makeup information may be a plurality of analog signals, each on a separate line and each controlling the degree of opening of a plurality of corresponding linear, solenoid operated valves.

In some embodiments, the solvent sources on lines 16, 18, etc. may be pressurized either by the application of above atmospheric pressure to each solvent reservoir or by the use of a pump connected to each of the solvent input lines 16, 18, etc.

A pair of back-pressure-independent, flow control systems 20 and 22 draw their inputs from the solvent composition makeup system 10. The output stream 14 from block 10 is split by a T connector 24 into two streams 26 and 28. These two streams are coupled to the inputs of the flow control systems 20 and 22.

Each of the flow control systems 20 and 22 is a positive displacement system which controls the output flow on lines 30 and 32 independently of back pressure exerted by the liquid chromatography columns 34 and 36 or other restrictions in the flow path. Column 36 need not be a chromatography column. It is only necessary that a structure substituting for column 36 substantially reproduce the characteristics of column 34 such as internal volume and mixing characteristics. Each of the flow control systems 20 and 22 receives control signals via a control bus 28 which defines the desired flow rate on output lines 30 and 32.

The structure of the flow control systems 20 and 22 can be any structure which insures that the flow rates on lines 30 and 32 are identical. The specific examples of the structures of these flow control systems will be described later herein. Any structure which can accept the desired flow rate signal on line 38 and can cause identical flow rates to occur on output lines 30 and 32 regardless of differences of back pressure and other flow restrictions on these lines will suffice for purposes of practicing the invention.

In FIG. 1 the sample flow path is at the top of the figure and the reference path is at the bottom of the figure. These two flow paths must have the same path length. The sample flow path includes a sample injector 40 of conventional design. The purpose of this unit is to inject the unknown sample composition entering the injector on line 42 into the incoming solvent composition stream on line 30 such that the sample is entrained in the input stream on line 44 to the liquid chromatography column 34. Normally, no sample injector 40 is found in the reference flow path since the purpose of the reference flow path is strictly to provide a reference signal for base line stabilization. Special applications could require a sample injector in the reference flow path. This reference signal is generated by detector 50 and is based solely on the characteristics of the solvent composition itself in line 32 after it emerges from the liquid chromatography column 36 or other device substituting for liquid chromatography column 36 on line 48. It is to be understood that references to first and second liquid chromatography columns made elsewhere herein also refer to a first liquid chromatography column in the path containing the sample and a second flow path simulating at least the path length of the liquid chromatography column as the reference flow path.

Detector 50 in both the sample and reference flow paths examines the characteristics of the emerging liquid streams on lines 48 and 52 from the liquid chromatography columns 34 and 36. Detector 50 may be either light absorbance type of detector or the refractive index type of detector. Any other form of detector used in liquid chromatography analysis may also be used. Suitable detectors include but are not limited to conductivity, electrochemical, infrared, photodiode array multi-wavelength, fluorescence, and the like. In the preferred embodiment, the detector 50 is either model number 8450 or 8490 available commercially from the assignee of the present invention.

The purpose of detector 50 is to detect the presence of individual components in the sample composition from line 42 as these individual components emerge at different times from the liquid chromatography column 34 and compare the responses to those of the reference flow path in line 48 and column 36. This detector detects these components by the changing light absorbance in the stream 52 or by the changing refractive index of this stream. Detector 50 outputs a signal on line 54 which is the difference between the optical characteristics of the stream in line 52 and the stream in line 48.

Since these optical characteristics may be varying because of variations in the input solvent composition on line 30, the signal on line 54 may have noise in it which can cause errors. The source of this noise is illustrated in FIGS. 2 and 3.

Figure 2:
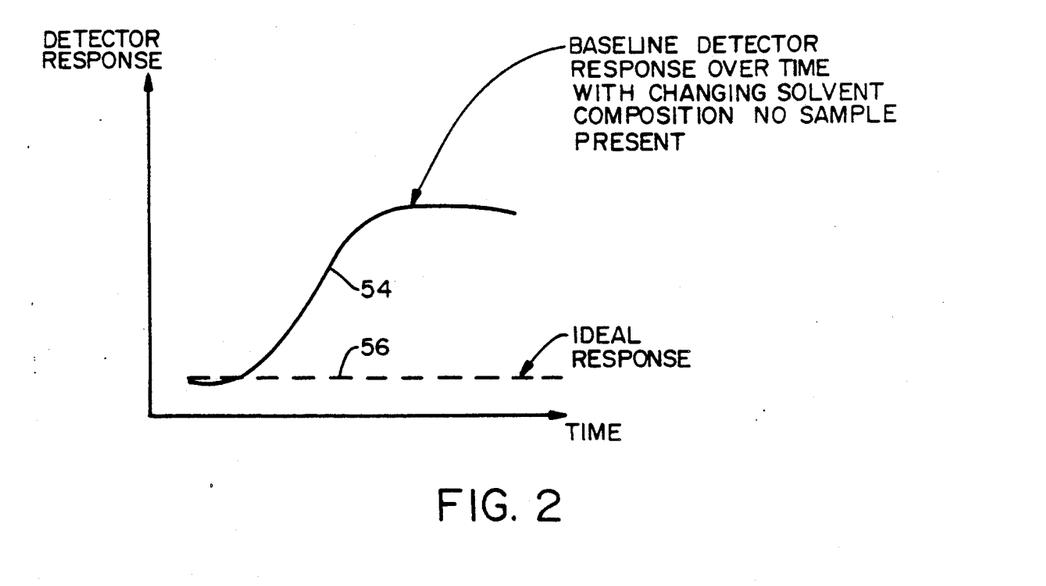
FIG. 2 is a sample plot of a detector baseline response of the output of either an absorbance detector or a refractive index detector over time when a perfectly formed gradient is slowly altered during the course of a run showing the effect of baseline drift caused by changing absorbance and changing refractive index as the solvent composition changes.
Figure 3:
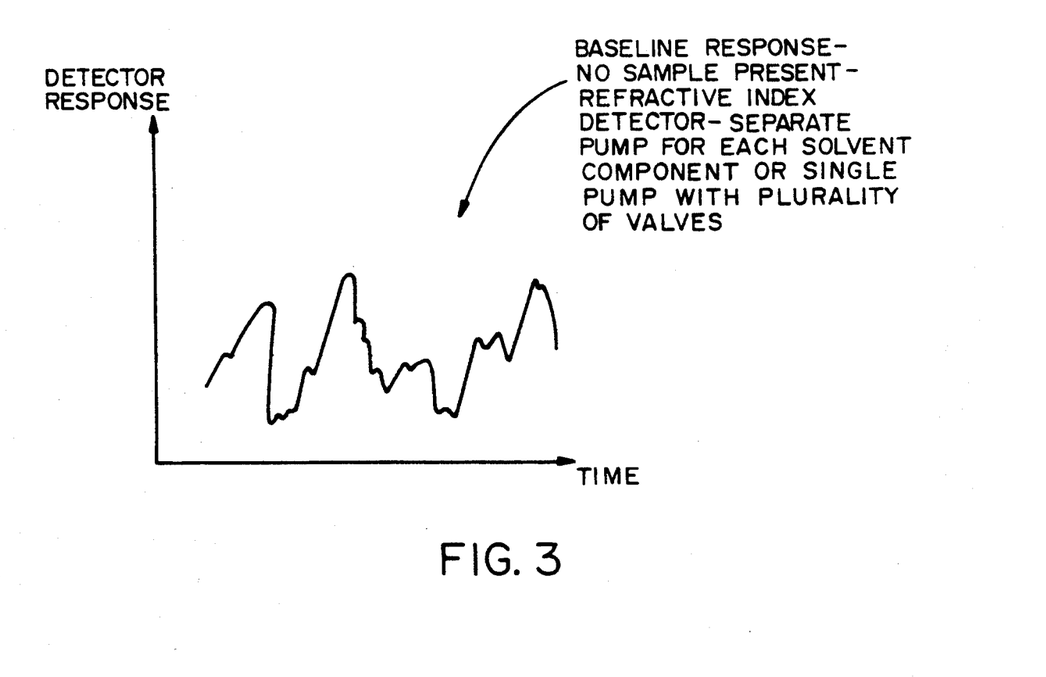
FIG. 3 is a sample plot of a refractive index detector baseline response with no sample present where either multiple separate pumps or a single pump with valves is used to make up the solvent composition.

FIG. 2 illustrates the baseline drift in detector response over time when a perfectly formed gradient solvent composition has its composition changed during the course of a run with no sample present. FIG. 2 represents the detector response to changes in both the refractive characteristics and the absorbance of the solvent composition standing alone with no injected sample as the solvent composition is slowly changed under the control of the user. A gradient means that the relative proportions of solvents 1, 2, 3, etc. are changing. Because both the refractive index and the light absorbance properties of the solvent composition changes when the relative proportion of its individual components change, it is seen from FIG. 2 that the baseline response of the detector to such a changing or gradient solvent composition is not a flat response but changes over time. Function 54 in FIG. 2 represents the baseline drift error caused by gradient solvent composition. Function 54 shows only the above stated source of error absent any other source of error such as non-repeatability in the solvent makeup process which is represented in FIG. 3 and is an independent source of error. The ideal flat baseline response is shown by the phantom line at 56.

With a changing baseline like that shown at 54, the characteristics of the baseline itself are "modulated", i.e., superimposed upon, the changes in the refractive index or absorbance caused by the various components of the sample as they emerge from the liquid chromatography column at different times. Since the only changes of interest are those changes caused by the presence of sample components in the output stream, having a changing baseline causes errors in correctly interpreting the optical characteristics of the output stream from the liquid chromatography column. If the effects of the changing baseline cannot be removed from the output of the detector so that only changes caused by the sample components are present, then gradient solvent compositions cannot be used. This is the case in the prior art with refractive index detectors. These refractive index detectors are extremely sensitive to changes in the solvent composition itself. Unless the solvent composition has a very stable makeup which does not change, a refractive index detector will inject noise into the output signal caused by the changes in the solvent composition.

In many prior art applications, the solvent composition is set and changed either by controlling the speed of individual motors which pump the various individual components or by controlling the timing of valves on a single pump. The solvents go into a mixer where they are mixed into the final solvent composition. Sometimes the mixer is omitted which can be an independent source of error where incomplete mixing results. Even when perfect mixing occurs, pumps or valves have errors which can cause another source of error. When using individual pumps for solvent makeup, the speeds of the motors and accuracy of pumping of each individual solvent component cannot be controlled closely enough with sufficiently repeatable accuracy to prevent errors. When using a single pump with valves, the lack of repeatability of the valves introduces errors. When using either individual pumps or a single pump with valves for solvent makeup, as is frequently done in the prior art, a baseline such as that shown in FIG. 3 often results. This source of baseline error is the slightly changing composition of the solvent even where gradients are not being used because of pumping or valve inaccuracies. These slight changes are reflected in the output signals of the detectors as baseline drift errors. This is especially true in the case where refractive index detectors are used since such detectors are extremely sensitive to the most minute of changes in the solvent composition. Thus, use of individual motors to pump each solvent component or a single pump with valves or a single pump with valves is unworkable to make up the solvent composition even where no gradient is to be used. The baseline drift error of the type shown in FIG. 3 will be superimposed upon the baseline drift of the type illustrated in FIG. 2.

Figure 4:
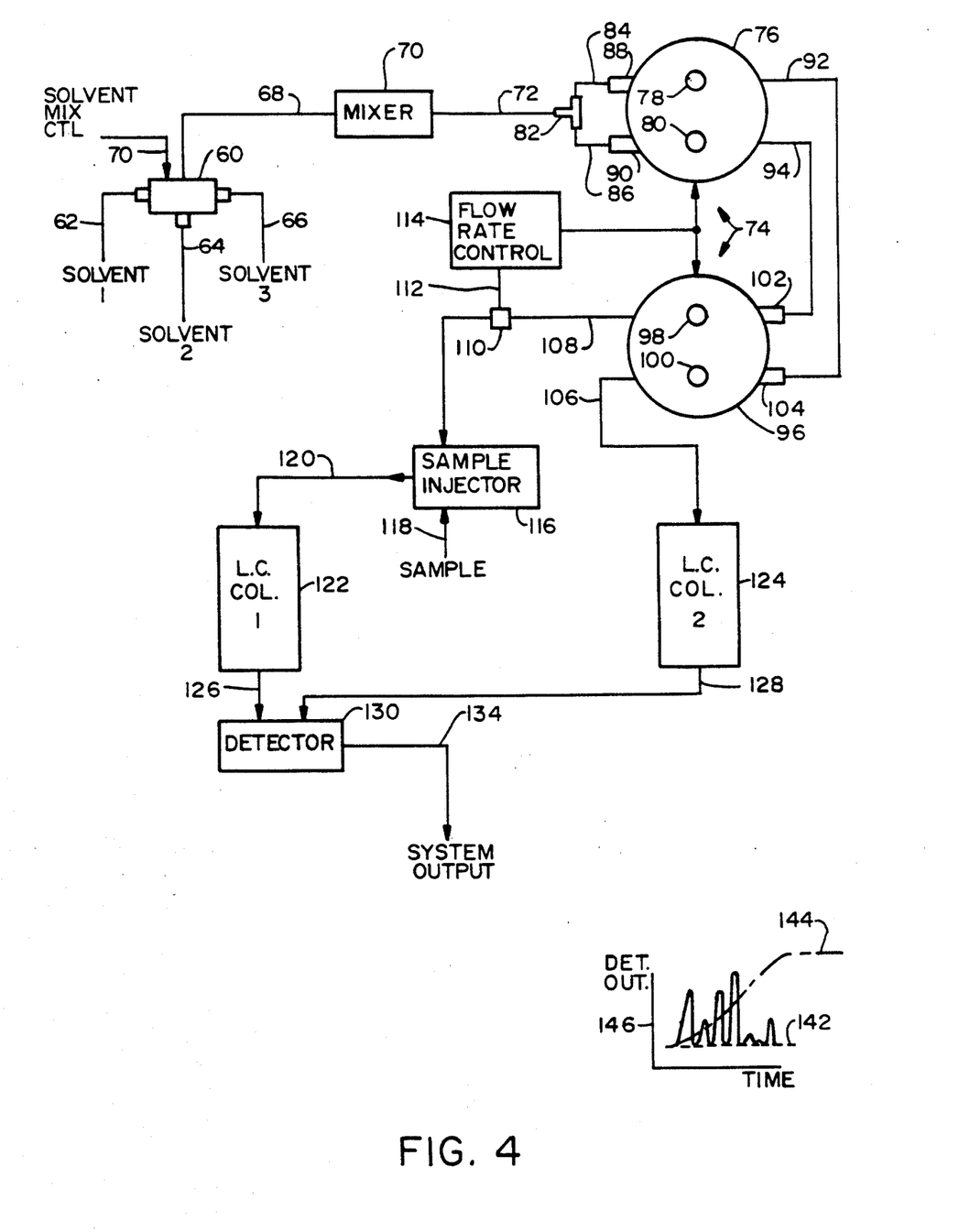
FIG. 4 is a block diagram of the preferred embodiment of the apparatus of the invention wherein a single pump is used with two pump heads, each pump head having two pistons, with both pump heads being driven by a single motor thereby causing two equal but independent flow rates to be achieved.

Referring to FIG. 4, there is shown a schematic diagram of the preferred embodiment of a dual flow liquid chromatography analysis system according to the teachings of the invention. Solvent composition makeup is provided by a mixing block 60 which is coupled by three input lines 62, 64, and 66 to three different solvent sources. Of course, more than three or less than three solvent sources may be used. The mixing block comprises a plurality of linear solenoid operated valves or other devices to control the relative amounts of each different solvent that are fed into output line 68. The relative proportion of each solvent is controlled by signals on the bus 70. The structure of the mixing block 60 is conventional, and any known solvent composition makeup structure will suffice for purposed of practicing the invention.

The solvent composition on line 68 is not always well mixed. Accordingly, an optional mixer 70 receives the solvent composition and mixes it thoroughly for output on the line 72.

To provide positive displacement and flow control on each of the separate flow paths, a pump 74 is provided. This pump is comprised of two separate pump heads in the preferred embodiment. An input pump head at 76 contains two input pistons 78 and 80. Each of these input pistons draws a separate stream of solvent through a T connection 82 coupled to the output of the mixer 70. These two input streams on lines 84 and 86 are drawn by the input pistons through two one-way input check valves 88 and 90. These check valves insure that when the input pistons 78 and 80 undergo their compression strokes, flow of solvent emerges from the pump head 76 on the output lines 92 and 94 and not on the input lines 84 and 86.

The pump 74 also has an output head 96 which contains two output pistons 98 and 100 in the preferred embodiment. These two output pistons draw their input solvent stream from the lines 92 and 94 through output check valves 102 and 104. These two output check valves insure that flow of solvent is in one direction only from lines 92 and 94 to output lines 106 and 108, respectively. Both pistons in each individual pump head are the same size and are driven at the same speed. The speeds of the pistons in the input pump head may be different from those in the output pump head. In addition, the input pistons 78 and 80, if driven by a cam, are driven either by the same cam or by two cams having identical profiles and turning at the same rate and indexed identically. The same statements are true for the output pistons 98 and 100.

A transducer 110 in output line 108 senses either the flow rate or the pressure in line 108 and provides a signal indicative thereof on line 112. Line 112 is a control input to a flow rate control system 114 which will be described in more detail below. The purpose of the flow rate control system 114 is to compare the actual flow rate to the desired flow rate and to control the driving system for the pistons so that the desired flow rate is achieved in both flow paths. Identity of flow rates automatically results because the pair of pistons 78 and 80 are the same size, run at the same speed and ride the cam profiles as defined above. The same comments hold for pistons 98 and 100. Any structure for the flow rate control system 114 that will achieve this result will suffice for purposes of practicing the invention. Suitable structures include but are not limited to analog flow rate control, digital flow rate control, combinations thereof, and the like.

Lines 108 and 106 symbolize the two separate flow paths of the liquid chromatography system. One of these flow paths, the one symbolized by line 108 is the sample flow path while the other, symbolized by line 106, is the reference flow path. Both flow paths should be of the same length for optimum performance. The sample flow path has the sample of unknown composition injected therein. This is accomplished by a conventionally designed sample injector 116 of conventional structure. The sample of unknown composition enters on line 118 and is entrained in the solvent composition entering via line 108. The output from the sample injector on line 120 is input to a first liquid chromatography column 122. The liquid chromatography column is of conventional design.

The reference flow solvent composition on line 106, without the sample injected therein, is passed through a second liquid chromatography column 124.

The flow rates in the lines 106 and 120 are caused by the flow rate control system to be the same regardless of whether the liquid chromatography columns 122 and 124 individually impose different back pressures resisting the flow of solvent therethrough. Accordingly, if the solvent composition in line 68 is changing for any reason, the very same changing solvent composition will emerge from the two liquid chromatography columns 122 and 124 on lines 126 and 128 simultaneously.

Detector 130 is used to detect the characteristics of the liquids in lines 126 and 128. Detector 130 may be any type of detector including a refractive index detector. Detector 130 detects not only the changes in the characteristics in the fluid in line 126 caused by the sample of unknown composition but also the changes caused by changes in the solvent composition itself. Detector 130 also detects the changes in the characteristics of the fluid in line 128 caused by changes in the solvent composition.

The detector 130 generates an output signal on line 134 which defines the changes in the characteristics of the fluids in lines 126 and 128, respectively. The output 134 is between fluid stream 128 and fluid stream 126. When there is no sample injected by the sample injector 116, the signal on line 134 will be a stable baseline like that shown at 142 in the sample plot of a typical detector output shown in the lower right hand corner of the figure. The dash-dot line 144 represents the base line which would result with no sample injected were it not for the use of two separate flow paths including a reference flow path. Thus, it can be seen that the presence of the second, i.e., reference flow path, causes the base line 142 to be made artificially flat. This results in changes on the detector output axis 146 resulting only from peaks caused by the components of sample as they emerge on the line 126.

The flow rate control unit 114 can take several different alternative embodiments. In the single pump embodiment shown in FIG. 4, the input head 76 and the output head 96 are both part of the same pump and are driven by the same motor and shaft. Therefore, the flow rate control unit 114 represents a conventional flow control circuit for such a pump. Such flow control systems are known and are commercially available from the assignee of the present invention in the form of the flow rate control system for the MINI-PUMP TM liquid chromatography pumping system. This control system is described in copending U.S. patent application APPARATUS FOR CONTROLLING A PUMP TO ACCOUNT FOR COMPRESSIBILITY OF LIQUIDS IN OBTAINING STEADY FLOW, by Honganen et al., Serial No. 913,356, filed 9/30/86. In fact, the pump 74 may be the MINI-PUMP liquid chromatography pump commercially available from the assignee if it is modified by adding an additional piston to each pump head. The pump heads may need to be enlarged for this modification since very high pressures are used in liquid chromatography systems which may lead to excessive generation of heat beyond the capacity of the MINI-PUMP pump heads to provide adequate cooling. Those skilled in the art of pump design will appreciate the modifications that need to be made to add an additional piston to each pump head. It is only necessary for purposes of practicing the invention that individual pumping action in each flow path be provided such that the flow rate in each flow path can be matched regardless of differences in the back pressure in each flow path. In the embodiment shown in FIG. 4, this automatically happens since both of the input pistons have the same size and are driven on the same shaft by the same cam configuration. The same is true for the output pistons 98 and 100. The output pistons are of the same size and are driven by the same motor shaft as the input piston 78 and 80. Therefore, the flow rate control system 114 merely needs to control the single pump motor for the desired flow rate in the line 108, and this flow rate will automatically be obtained in line 106 by virtue of the fact that the pistons driving fluid through line 106 are the same size as the pistons driving fluid through the line 108.

Figure 5:
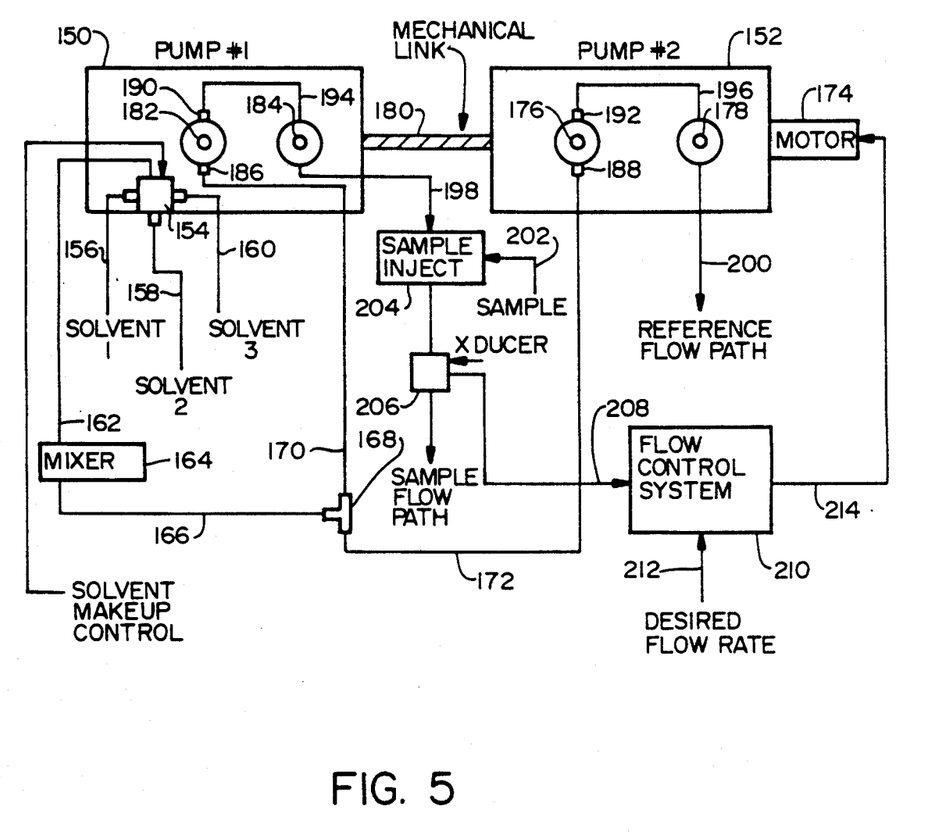
FIG. 5 is a block diagram of an alternative embodiment of the apparatus of the invention wherein two pumps are used, each pump having two pump heads, each pump head having a single piston and wherein each pump is mechanically linked to the other pump such that a single motor drives all pistons in both pumps at the same speed.

FIG. 5 illustrates an alternative two pump embodiment with a mechanical linkage between the pumps so that a single motor drives both pumps at the same speed. In this embodiment a first pump 150 may be a MINI-PUMP liquid chromatography pump or it may be any other liquid chromatography pump which is capable of achieving the desired flow rate and capable of being mechanically linked to the drive shaft of another liquid chromatography pump 152. The second pump 152 may be of the same design as pump 150 or a different design. It is only necessary in the embodiment shown in FIG. 5 that each pump be capable of delivering the desired flow rate that the two pumps be capable of being mechanically driven by the same motor such that both pumps deliver identical flow rates in the two flow paths independent of differences in back pressure when driven at the same speed. A solvent makeup block 154 has three inputs 156, 158, and 160 which are coupled to the sources of three different solvents. Of course, more than three solvents or less than three solvents may also be used by suitable alteration of the solvent makeup block valving mechanism. As in the case of the embodiment shown in FIG. 4, solvents one, two and three may be pumped or may be pressurized. However, it will be appreciated that solvent one, two and three may be at atmospheric pressure and not pumped or pressurized.

The output from the solvent composition makeup block on line 162 is fed to a conventional mixer 164. The output of this mixer on line 166 is coupled to a T connector 168. This T connection splits the stream of solvent on line 166 into two flow segments on lines 170 and 172. Line 170 is coupled to the input of pump 150. Line 172 is coupled to the input of pump 152. The flow rate in both lines 170 and 172 will be the same because each of the pumps is pumping at the same flow rate.

A single motor 174 drives pump 152. This motor drives two cams (not shown) in pump 152. One cam drives an input piston 176 and the other cam drives an output piston 178. The cams may have different profiles, but both are driven at the same rotational speed.

A mechanical link 180 is coupled to and rotates with the cams which drive the input pistons 176 and 178 of pump 152. Mechanical link 180 is coupled to two cams (not shown) in pump 150. One cam drives an input piston 182 and the other cam drives an output piston 184. The cam that drives the input piston in pump 150 has the same profile and is indexed identically as the cam that drives the input piston in the pump 152.

The two input pistons 176 and 182 draw solvent from lines 170 and 172 in at the same rate through input check valves 186 and 188. Both of these input pistons pump solvent out through output check valves 190 and 192 to output pistons 184 and 178, respectively. The check valves 186, 190, 188, and 192 insure that solvent flow is unidirectional in each of the pumps in the stated direction. The output pistons 184 and 178 receive solvent from the input pistons via lines 194 and 196, respectively. These output pistons then pump solvent out through the sample flow path 198 and the reference flow path 200.

The sample flow path has sample of unknown composition on line 202 injected therein by a sample inject block 204. A transducer 206 senses flow conditions in the sample flow path and outputs a signal on line 208 to a flow control system 210. The flow control system receives a flow control signal on line 212 regarding the desired flow rate. The flow control system then calculates the actual flow rate as indicated by the signal on line 208, and compares the actual flow rate to the desired flow rate to generate an error signal which is used to control the motor 174 via line 214. Although flow conditions are only sensed in the sample flow path 198, since pumps 150 and 152 are driven by the same shaft, the same flow rate will result in both the sample flow path and the reference flow path regardless of different flow restrictions in each path.

Figure 6:
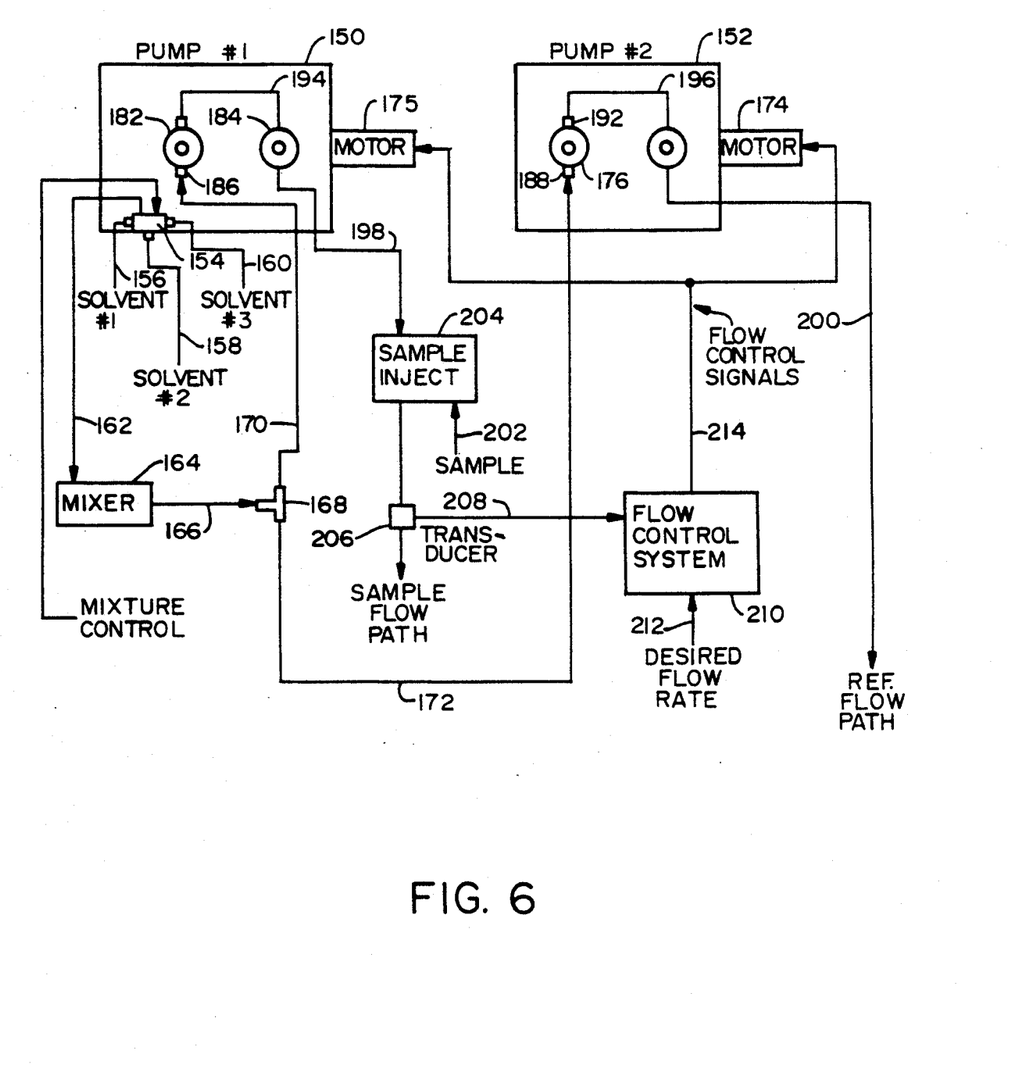
FIG. 6 is a block diagram of another alternative embodiment of the invention wherein two pumps are used with each pump having a pair of pump heads, each pump head having a single piston and wherein each pump is driven by the same flow control system.

Referring to FIG. 6, there is shown an alternative embodiment of the system of the invention. In FIG. 6 the various elements have the same purpose and function as the elements with the same numbers in the embodiment shown in FIG. 5. The only difference between the embodiments of FIG. 6 and FIG. 5 is that in FIG. 6 there is no mechanical linkage between the first and second pumps 150 and 152, respectively. Equal flow rates in the sample flow path 198 and the reference flow path 200 are achieved using a single flow control system 210 which compares the desired flow rate signal on bus 212 to the actual flow rate in the sample flow path as transmitted on line 208 by a transducer 206. The flow control system can be the same known structure defined in the above cited U.S. patent application which is hereby incorporated by reference. The flow control system then compares the actual flow rate to the desired flow rate and generates an error signal on bus 214 which is used to control a motor 174 driving pump 152 and a motor 175 driving pump 175. In the preferred version of this embodiment, pumps one and two are MINIPUMPs and are commercially available from the assignee of the present invention. The motors 174 and 175 are stepper motors. The flow control system 210 and the flow control signals on the bus 214 as well as the feedback signal from the sample flow path transducer 206 are as described in above cited U.S. patent application.

Because both motors are driven with the same control signals, each motor drives its pump at the same speed. Because the pumping pistons and each of the cylinders are the same size and are being driven at the same speed with identical cam profiles for corresponding pistons in each pump, equal flow rates are achieved in the sample flow path and the reference flow path.

Although the invention has been described in terms of the preferred and alternative embodiments disclosed herein, those skilled in the art will appreciate numerous other modifications which may be made without departing from the teachings of the invention. All such modifications are intended to be included within the scope of the claims appended hereto.

What is claimed is:

1. An apparatus for stabilizing the baseline response of a chromatography system comprising:
   supply means for making up a solvent composition from one or more solvents;
   a detector means having a first fluid input and a second fluid input for detecting the difference in a selected characteristic between the fluid in a stream entering said first fluid input and the fluid in a stream entering said second fluid input;
   a first fluid flow path from said supply means to said detector means first input having a flow path length;
   a second fluid flow path from said supply means to said detector means second input having a flow path length which is identical to the flow path length of a said first fluid flow path;
   a liquid chromatography column in said first fluid flow path having a defined set of column parameters including resistance to flow;
   reference means in said second fluid flow path for substantially reproducing at least the resistance to flow parameter of said liquid chromatography column;
   sample injection means for receiving a sample of unknown composition and injecting said sample into a solvent stream received at an input and coupled to said first fluid flow path such that said sample is injected in said first fluid flow path and having an output coupled to said first liquid chromatography column;
   first pumping means in said first fluid flow path and coupled to said sample injection means for forcing solvent received from said supply means through said first liquid chromatography column at a selected flow rate regardless of the amount of resistance to flow caused by said first liquid chromatography column;
   second pumping means in said second fluid flow path for forcing solvent received from said supply means through said reference means at a substantially identical flow rate as exists in said first fluid flow path regardless of differences in resistance to flow caused by said reference means said first and second pumping means being located at positions in the first and second flow paths that are not common to both the first and second flow paths.

2. The apparatus of claim 1 wherein said reference means is a second liquid chromatography column.

3. The apparatus of claim 2 wherein said first means for forcing and said second means for forcing are the same pump with two individual but synchronized and identical capacity pumping apparatus and output paths one said output path coupled to said first fluid flow path and the other output path coupled to said second fluid flow path.

4. The apparatus of claim 2 wherein said first and second means for forcing a selected flow rate are separate pumps having identical pumping capacity when run at the same speed, each coupled to the other by a shared drive shaft such that each said pump being driven at the same speed by said shared drive shaft, said shared drive shaft being driven by a common power source.

5. The apparatus of claim 4 wherein said pumps have piston sizes which are equal.

6. The apparatus of claim 1 wherein said first and second means are separate pumps pumping at substantially the same flow rate, and wherein each said pump has a separate drive motor, each said drive motor being driven by a shared control system so as to obtain substantially identical flow rates in each flow path regardless of differences in resistance to flow in said first and second flow paths.

7. The apparatus of claim 6 wherein said separate pumps have pistons of identical size.

8. The apparatus of claim 7 wherein said shared control system comprises means for sensing the pressure at the input of said first liquid chromatography column and for converting this pressure into a flow rate and for comparing this flow rate to a desired flow rate and for generating a control signal which is sent to each motor for controlling the speed thereof.

9. An apparatus for performing liquid chromatography comprising:
    a first liquid chromatography column having in a first flow path having a flow path length and a resistance to flow therethrough;
    means for substantially reproducing the path length and resistance to flow of said first liquid chromatography column in a second flow path;
    first positive displacement means in said first flow path for pumping a first stream of solvent through said first flow path with a selected flow rate even if changes in the resistance to flow occur in said first flow path, said first stream having entrained therein sample having at least some unknown characteristics;
    second positive displacement means for pumping a second stream of said solvent through said second flow path at a flow rate which is substantially identical to the flow rate in said first flow path caused by said first positive displacement means, said first and second positive displacement means being located at positions in the first and second flow paths that are not common to both the first and second flow paths;
    detection means for determining the difference in one or more selected characteristics of said first and second streams of fluid as they emerge from said first and second flow paths.

10. The apparatus of claim 9 further comprising a solvent makeup means coupled to sources of a plurality of different solvents and having an input for receiving solvent composition makeup information for combining solvents from said plurality of sources in accordance with said solvent composition makeup information and outputting said composite solvent to said means for pumping.

11. The apparatus of claim 10 wherein said makeup means is also for selectably changing the relative proportions of at least some of the solvents in the final solvent composition over time.

12. The apparatus of claim 10 wherein said detection means includes a refractive index detector for examining the refractive index of said first and second solvent streams, respectively, and for generating signals indicative thereof, and further comprising difference means coupled to said refractive index detector output signals for determining the difference between the characteristics of said first and second streams and for outputting a signal indicative of the difference between said first and second solvent streams.

13. The apparatus of claim 12 wherein said solvent composition makeup means includes a plurality of pumps, each pump having an input coupled to one source of solvent, and each pump coupled to a control means for running each pump at a speed relative to the speeds of the other pumps such that the amount of each particular solvent pumped into the output stream of the solvent composition makeup means includes the desired proportion of each said solvent.

14. The apparatus of claim 13 wherein said means in each of said first and second flow paths for pumping comprises a single pump having first and second pump heads, said first pump head having formed therein first and second input cylinders in which reside first and second reciprocating input pistons said first input piston pumping fluid in said first flow path and said second input piston pumping fluid in said second flow path, respectively, said second pump head having formed therein first and second output cylinders in which first and second reciprocating output pistons reside, said first output piston coupled to said first input piston and pumping fluid in said first flow path, and said second output piston coupled in said second input piston and pumping fluid in said second flow path, respectively, and each of said input pistons running on a cam having a contour each substantially the same flow rate is achieved in said first and second flow paths, and each of said output pistons running on a cam having a contour such that identical flow rates are achieved in said first and second flow paths, each of said cams driven by drive means which drive said cams at the appropriate rotational speed to achieve substantially identical flow rates for each first and second flow paths, each of said input piston/cylinder combinations being coupled to said solvent composition makeup means through first and second check valves, respectively, and each of said output piston/cylinder combinations being coupled to one of said input piston/cylinder combinations through first and second check valves.

15. The apparatus of claim 13 wherein said means in each of said first and second flow paths for pumping comprises first and second pumps having identically sized pistons and identically contoured cam shafts driving said pistons and coupled so as to be driven at the same speed, said first pump having its output coupled to said first liquid chromatography column and said second pump having its output coupled to said second liquid chromatography column.

16. The apparatus of claim 15 wherein each of said first and second pumps is coupled to the same drive shaft so as to be driven at the same speed from the same power source.

17. The apparatus of claim 15 wherein each of said first and second pumps is driven by a separate motor and further comprising a flow rate control system coupled so as to determine the flow rate in one of said liquid chromatography columns and to control both said motors so that both said pumps run at speeds such that the flow rates in each said liquid chromatography column are identical.

18. The apparatus of claim 13 wherein said means in each of said first and second flow paths for pumping comprises first and second pumps and coupled so as to be driven at a speed for each pump such that the flow rate of liquid in the output stream for each pump in said first and second flow paths is identical, said first pump having its output coupled to said first liquid chromatography column and said second pump having its output coupled to said second liquid chromatography column.

19. An apparatus comprising:
   first and second liquid chromatography columns in first and second flow paths having substantially identical flow path length and back pressure characteristics;
   means in each of said first and second flow paths at a point which is not common to said first and second flow paths for pumping first and second streams of solvents through said first and second liquid chromatography columns with substantially identical flow rates even if the resistance to flow caused by either said first or said second liquid chromatography column is different or changes relative to the resistance to flow caused by the other of said liquid chromatography columns, one of said streams having entrained therein sample having at least some unknown characteristics; and
   detection means for determining the differences in the characteristics of said first and second streams as they emerge from said first and second liquid chromatography columns.

* * * * *